United States Patent
Trakas

(10) Patent No.: US 9,084,572 B2
(45) Date of Patent: Jul. 21, 2015

(54) COLLAPSIBLE LARYNGOSCOPE

(71) Applicant: Michael J. Trakas, Tucson, AZ (US)

(72) Inventor: Michael J. Trakas, Tucson, AZ (US)

(*) Notice: Subject to any disclaimer, the term of this patent is extended or adjusted under 35 U.S.C. 154(b) by 445 days.

(21) Appl. No.: 13/664,238

(22) Filed: Oct. 30, 2012

(65) Prior Publication Data

US 2013/0109923 A1     May 2, 2013

Related U.S. Application Data

(60) Provisional application No. 61/544,376, filed on Nov. 1, 2011.

(51) Int. Cl.
| A61B 1/267 | (2006.01) |
| A61M 16/04 | (2006.01) |
| A61B 17/24 | (2006.01) |

(52) U.S. Cl.
CPC .............. *A61B 1/267* (2013.01); *A61B 17/24* (2013.01); *A61M 16/0488* (2013.01); *A61M 16/0493* (2014.02); *A61M 16/0495* (2014.02)

(58) Field of Classification Search
CPC ........ A61B 1/267; A61B 1/0052; A61B 1/24; A61B 17/24; A61M 16/04; A61M 16/0488; A61M 16/049; A61M 16/0493; A61M 16/0495; A61M 16/0497
USPC .................. 600/194–197, 190, 193, 185, 187, 600/239–240; 606/106, 108; 433/136, 137, 433/138, 140; 128/207.14, 200.26
See application file for complete search history.

(56) References Cited

U.S. PATENT DOCUMENTS

| 252,127 | A * | 1/1882 | Morrill .................. 600/240 |
| 3,930,507 | A * | 1/1976 | Berman ............. 128/207.14 |
| 4,570,614 | A | 2/1986 | Bauman |
| 4,573,451 | A | 3/1986 | Bauman |
| 4,878,486 | A | 11/1989 | Slater |
| 4,958,624 | A | 9/1990 | Stone et al. |
| 5,355,870 | A | 10/1994 | Lacy |
| 5,879,304 | A | 3/1999 | Shuchman et al. |
| 5,888,195 | A | 3/1999 | Schneider |
| 5,938,591 | A | 8/1999 | Minson |
| 6,139,491 | A | 10/2000 | Heine et al. |
| 6,251,069 | B1 * | 6/2001 | Mentzelopoulos et al. .. 600/196 |

(Continued)

FOREIGN PATENT DOCUMENTS

| EP | 0184588 A1 | 6/1986 |
| EP | 1062905 A1 | 12/2000 |

(Continued)

*Primary Examiner* — Todd Manahan
*Assistant Examiner* — Marcela I Shirsat
(74) *Attorney, Agent, or Firm* — Richard C Litman

(57) ABSTRACT

The collapsible laryngoscope includes a substantially U-shaped frame having an open proximal end and a closed distal end, the proximal and distal ends being raised with respect to a central portion thereof to form a substantially saddle-shaped frame. A bite block is secured to the proximal end of the frame, fixing the proximal end. A distal end of a flexible rib is secured to the distal end of the frame, the proximal end of the flexible rib being positioned adjacent the bite block. An elastomeric sheath is secured to and covers the substantially U-shaped frame and the upper surface of the central portion of the flexible rib. A strap or the like is secured to the proximal end of the flexible rib for lifting the central portion of the flexible rib with respect to the substantially U-shaped frame. The flexible rib is then selectively locked in this deployed, lifted position.

18 Claims, 3 Drawing Sheets

(56) References Cited

U.S. PATENT DOCUMENTS

| | | | |
|---|---|---|---|
| 8,142,353 B2 | 3/2012 | Pecherer et al. | |
| 8,414,481 B2* | 4/2013 | Hakanen et al. | 600/196 |
| 8,684,919 B2* | 4/2014 | Anca et al. | 600/239 |
| 2002/0117171 A1* | 8/2002 | Parker | 128/200.26 |
| 2005/0240081 A1 | 10/2005 | Eliachar | |
| 2006/0247496 A1* | 11/2006 | Tjong Joe Wai | 600/184 |
| 2012/0190929 A1 | 7/2012 | Patel et al. | |

FOREIGN PATENT DOCUMENTS

| | | |
|---|---|---|
| GB | 2481515 A | 12/2011 |
| WO | WO 03041570 A2 | 5/2003 |

\* cited by examiner

COLLAPSIBLE LARYNGOSCOPE

CROSS-REFERENCE TO RELATED APPLICATION

This application claims the benefit of U.S. Provisional Patent Application Ser. No. 61/554,376, filed Nov. 1, 2011.

BACKGROUND OF THE INVENTION

1. Field of the Invention

The present invention relates to laryngoscopy, and particularly to a collapsible laryngoscope for endotracheal intubation and the like.

2. Description of the Related Art

Laryngoscopy is a medical procedure that is used to obtain a view of the vocal folds and the glottis of a patient. Laryngoscopy may be performed to facilitate tracheal intubation during general anesthesia, or for cardiopulmonary resuscitation, or for procedures on the larynx or other parts of the upper tracheobronchial tree.

Direct laryngoscopy is typically carried out with the patient lying on his or her back. The laryngoscope is inserted into the mouth on the right side and flipped to the left to trap and move the tongue out of the line of sight, and depending upon the type of blade used, may be inserted either anterior or posterior to the epiglottis and then lifted with an upwards and forward motion, away from the user and towards the floor of the patient's mouth. This move makes a view of the glottis possible. Laryngoscopy is extremely uncomfortable and is not typically performed on conscious patients, or on patients with an intact gag reflex.

FIG. 3 illustrates use of a conventional laryngoscope 100 having a curved or "Macintosh" type blade 104, which is joined to a handle 102. As shown, the Macintosh blade 104 is positioned in the vallecula V anterior to the epiglottis E and just behind the root of the patient's tongue 108, lifting the epiglottis E out of the visual pathway. This allows an endotracheal tube 106 or the like to be fed through a channel 110 defined in the curved blade 104 into the patient's trachea T. The channel 110, however, provides limited access to the patient's trachea 1, having dimensions not much greater than the typically small endotracheal tube 106. Further, as is well known, it can be extremely difficult to properly view the glottis opening and position the distal end of blade 104 in the vallecula V, thus making it extremely difficult to gain access to the trachea T. This difficulty in viewing the vocal cords is often due to misaligned oropharyngeal, pharyngeal and laryngeal axes, retrognathia (i.e., the inability to prognath the jaw), long upper incisors, decreased submental compliance, and redundant oropharyngeal tissue (e.g., a large tongue, tonsils, etc.), pharyngeal tissue (e.g., pharyngeal adipose pads), and similar conditions. Additionally, the simultaneous use of a conventional oxygen mask of the type used with bag and mask ventilation, as in anesthesia circuits, and a conventional laryngoscope 100 having a handle 102 is not possible. With regard to the latter consideration, bag and mask ventilation with such a system is a necessary option in many procedures, but is impossible with conventional scope 100 due to the obstruction caused by handle 102 protruding from the mouth. It would obviously be desirable to provide a laryngoscope which can be placed in the oral airway, following induction of anesthesia, which could be used simultaneously with bag and mask ventilation, providing a channel for fresh gas flow and the exchange of expired gases until intubating conditions are met. For this reason, it is desirable to provide a laryngoscope which does not protrude from the mouth of the patient when it is in use.

Thus, a collapsible laryngoscope solving the aforementioned problems is desired.

SUMMARY OF THE INVENTION

The collapsible laryngoscope includes a substantially U-shaped frame having an open proximal end and a closed distal end, the proximal and distal ends of the frame being raised with respect to a central portion thereof to form a substantially saddle-shaped frame. A bite block is secured to the proximal end of the substantially U-shaped frame, fixing the open proximal end. A flexible rib having opposed proximal and distal ends extends between a pair of side ribs defined by the frame. The distal end of the flexible rib is secured to the distal end of the substantially U-shaped frame. The proximal end of the flexible rib is positioned adjacent the bite block.

An elastomeric sheath is secured to and covers the substantially U-shaped frame and an upper surface of the central portion of the flexible rib. A strap or the like is secured to the proximal end of the flexible rib for lifting the central portion of the flexible rib with respect to the substantially U-shaped frame. The flexible rib is then selectively locked in this deployed, lifted position.

In use, the substantially U-shaped frame is inserted into a patient's oral cavity with the flexible rib in a collapsed state, the central portion thereof being aligned with the central portion of the substantially U-shaped frame. The flexible rib is then lifted with respect to the substantially U-shaped frame by pulling on the strap, such that the elastomeric sheath and the flexible rib press against the patient's tongue and oropharyngeal tissue, the substantially U-shaped frame pressing against the patient's hard palate. In this deployed configuration, the elastomeric sheath defines an open channel beneath the flexible rib for insertion of an endotracheal tube or the like.

Further, as is well known in laryngoscopy, it should be understood that the present collapsible laryngoscope may be used in combination with a variety of other related tools, such as a light, still or video cameras, fiber optics and/or other associated optics, or a handle portion.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
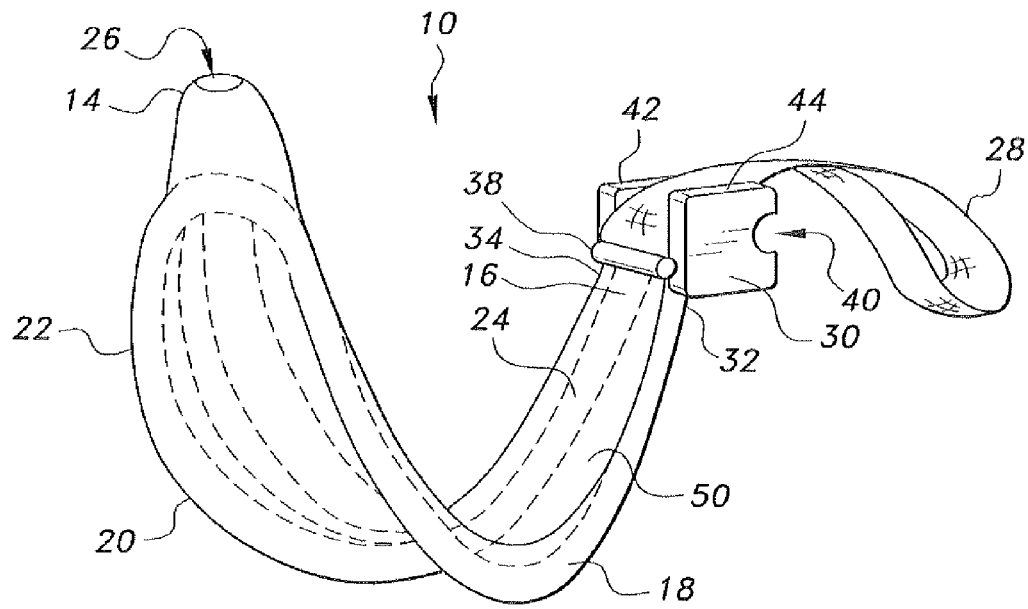
FIG. 1 is a perspective view of a collapsible laryngoscope according to the present invention, shown in a collapsed state.
Figure 3:
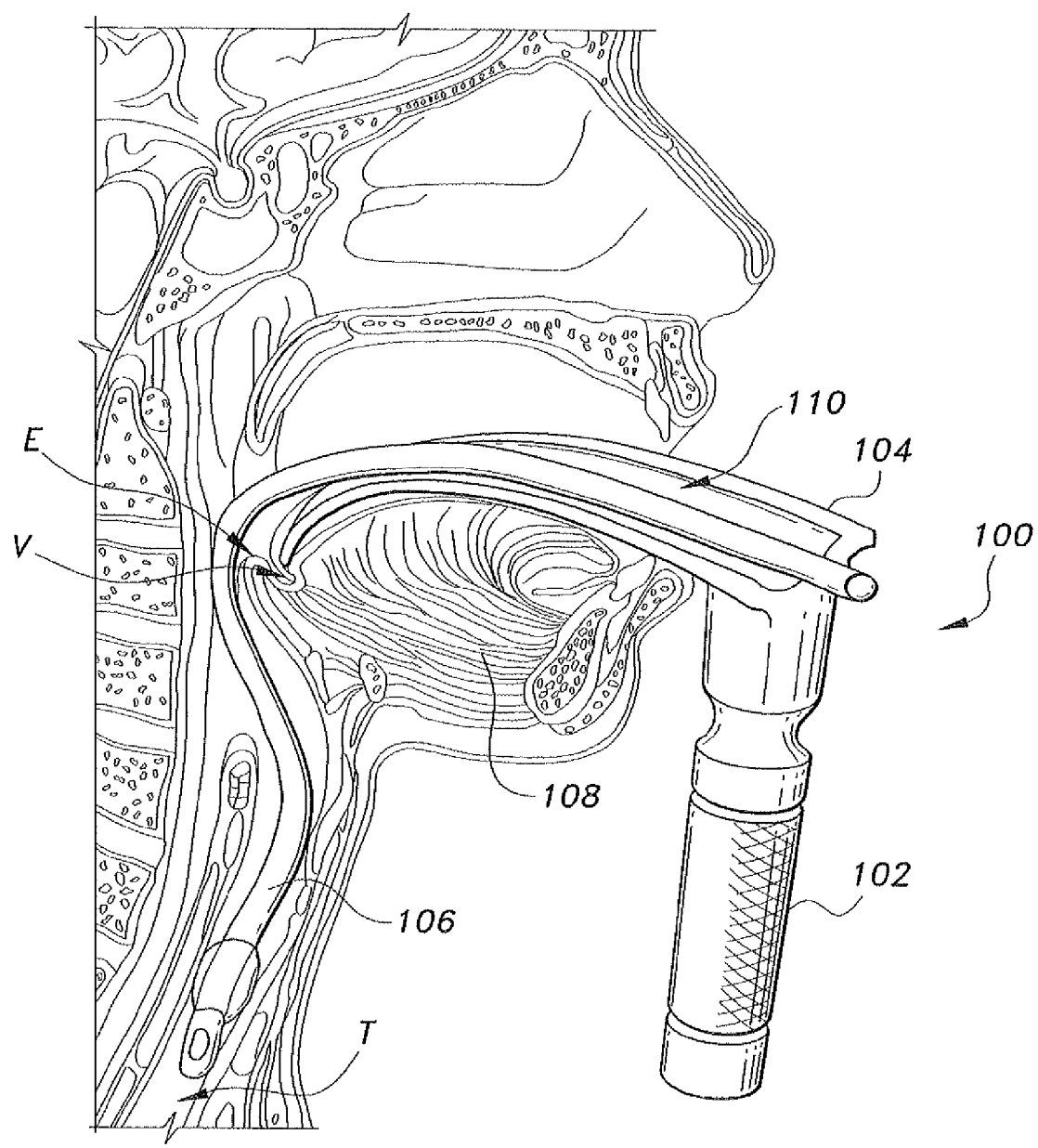
FIG. 3 illustrates the positioning and use of a Macintosh laryngoscope blade according to the prior art.

In contrast to the conventional prior art laryngoscope blade 104 of FIG. 3, which remains in a fixed and static configuration, the present collapsible laryngoscope 10 is adjustable between a collapsed and a deployed state. FIG. 1 illustrates the collapsible laryngoscope 10 in the collapsed state. A rigid frame 22 is formed from a pair of substantially U-shaped rigid ribs 18, 20, extending parallel to each other and joined to one another at their respective distal ends. The proximal ends 32, 34 of the rigid ribs 18, 20, respectively, are secured to laterally opposing sides of a bite block 30. The rigid frame 22 has a substantially saddle-like shape. A flexible rib 24 extends between the ribs 18, 20. The distal end 14 of the flexible rib 24 is mounted to the distal end of the rigid frame 22. The proximal end 16 of the flexible rib 24 is secured to a deployment strap 28, and extends between the two laterally opposed side walls 42, 44 of bite block 30. Preferably, the flexible rib 24 has an air passageway 26 defined therethrough, as shown, allowing the flexible rib 24 to be used for oxygenation and ventilation of the patient when the laryngoscope 10 is in the collapsed state. A resilient and flexible sheath 50 covers the rigid frame 22 and the flexible rib 24, as shown. The sheath 50 is preferably formed from an elastomeric material.

Figure 2:
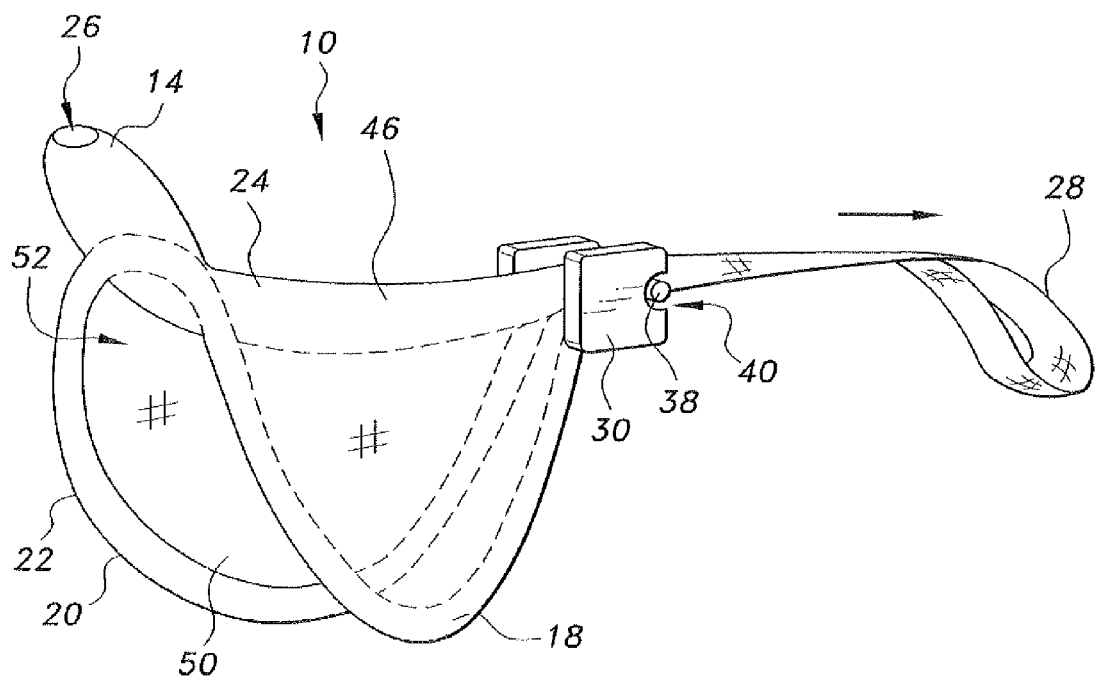
FIG. 2 is a perspective view of the collapsible laryngoscope of FIG. 1, shown in a deployed state.

The laryngoscope 10 is positioned within the patient's mouth in the collapsed state of FIG. 1. FIG. 2 illustrates the laryngoscope 10 in its deployed state. Once fitted within the patient's mouth, the deployment strap 28 is pulled toward the medical practitioner (i.e., away from the patient's throat). This pulls the proximal end 16 of the flexible rib 24 toward the medical practitioner, between the walls 42, 44 of the bite block 30, raising the central portion 46 of the flexible rib 24 upward. As shown in FIG. 1, in the collapsed state, the central portion 46 of the flexible rib 24 extends between the ribs 18, 20, following their substantially U-shaped contours. When the deployment strap 28 is pulled, as in FIG. 2, the rigid ribs 18, 20 remain in their initial position and the central portion 46 is raised upward as the distal end 16 is pulled back out of the patient's mouth. The sheath 50 covers the upper end of the flexible rib 24. Thus, a central portion of the sheath 50 is similarly lifted, as shown in the deployed configuration of FIG. 2.

In the deployed configuration of FIG. 2, the elastomeric sheath 50 and the flexible rib 24 press against the patient's tongue and oropharyngeal tissue, while the substantially U-shaped frame 22 presses against the patient's hard palate. In this deployed configuration, the elastomeric sheath 50 defines an open channel 52 beneath the flexible rib 24 for insertion of an endotracheal tube or the like. Deployment of the flexible rib 24 defines the channel 52 beneath the elastomeric sheath 50 from the patient's mouth to the patient's larynx by displacing the tongue and oropharyngeal tissue away from the channel 52, thus allowing direct or indirect visualization of the oropharynx, pharynx, larynx and vocal cords. The channel 52 remains open for solids, liquids, or gasses to pass therethrough. In the deployed state, the channel 52 also allows for nasal intubation, in which an endotracheal tube or breathing tube is placed in a nostril, where it travels through the nasopharynx, beneath the soft palate and uvula, then into the oropharynx through the channel 52, which displaces the oropharyngeal tissue, and then into the larynx, beyond the vocal cords, and into the trachea.

A laterally extending pin 38 is preferably secured to the proximal end 16 of the flexible rib 24. As shown in FIG. 1, in the collapsed state, the pin 38 rests against or adjacent to the distal end of bite block 30. However, when the deployment strap 28 is pulled, as shown in FIG. 2, the pin 38 is moved longitudinally along with the proximal end 16 of flexible rib 24, and may be received within notches 40 formed in the proximal edges of the sidewalls 42, 44 of the bite block 30, thus locking the flexible rib 24 in the deployed configuration of FIG. 2. It should be understood that any other suitable type of releasable locking mechanism may be used for selectively locking the flexible rib 24 in the deployed, lifted position.

The sheath 50 is preferably formed from a relatively thin, flexible material, covering the rigid frame 22 and flexible rib 24, conforming to the contour of frame 22 in the collapsed state of FIG. 1. In the deployed state of FIG. 2, the sheath 50, being stretched and lifted by the flexible rib 24, defines the channel 52. The sheath 50 provides a flexible outer covering for the frame 22 and the flexible rib 24, protects the frame 22 and the flexible rib 24 from coming into direct contact with the patient, and pushes away the redundant tissue of the oropharynx of the patient to define the channel 52. When deployed, the sheath 50 keeps oropharyngeal tissue from entering the channel 52, and the channel 52 provides the medical practitioner with access to the trachea, thus replacing the limited access provided by the channel 110 of the conventional blade 104 of the prior art laryngoscope 100 of FIG. 3.

Figure 4:
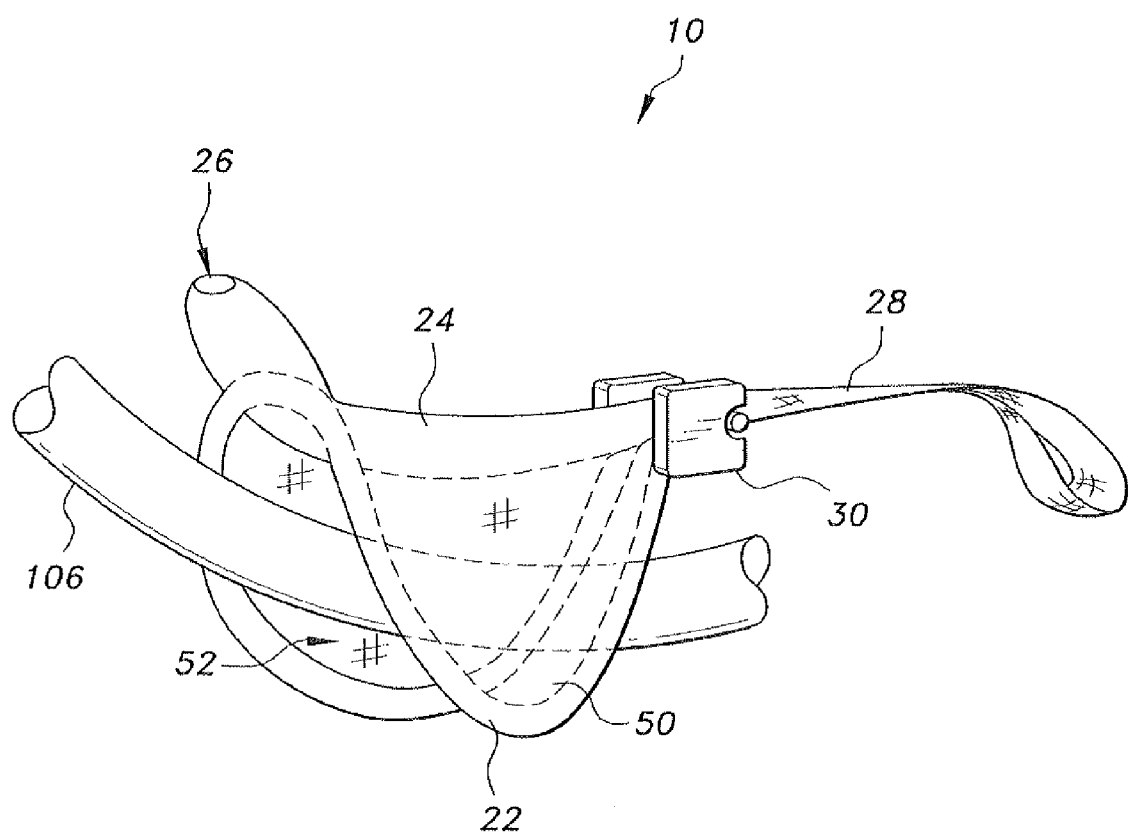
FIG. 4 is an environmental perspective view of the collapsible laryngoscope of FIG. 2, shown in a deployed state and illustrating positioning of an exemplary endotracheal tube through the laryngoscope.

As shown in FIG. 4, the channel 52, defined by the sheath 50, provides ample adjustable room for the insertion and passage of the exemplary endotracheal tube 106. Once the laryngoscope 10 is inserted in the oral cavity and deployed, the endotracheal tube 106 is inserted through the channel 52. Once the endotracheal tube 106 is placed, it is free to move with respect to the laryngoscope 10, as the channel 52 is defined by an open bottom end. This allows the laryngoscope 10 to be collapsed and removed from the oral cavity easily and without pinching or moving the tube 106, or having to slide the laryngoscope 10 along the length of the tube 106. The channel 52 is closed in response to the laryngoscope 10 being placed in the collapsed state, although, as shown in FIG. 1, even in the collapsed configuration, air and solids are still free to pass from the mouth to the trachea.

It should be understood that the sheath 50 shown in FIGS. 1 and 2 is shown for exemplary purposes only, and that the sheath 50 may vary in contour or configuration, and may be inflatable, detachable from the frame 22, or disposable, for example. The sheath 50 may be formed from any suitable type of material, such as fabric, plastic, flexible medical materials, or may be formed from an autoclavable material. Similarly, the flexible rib 24 may be formed from any suitable type of flexible material. As a further alternative, the flexible rib 24 may be formed from a material that becomes rigid upon lifting or expansion. As an alternative to the deployment of the flexible rib 24 via the strap 28, the flexible rib 24 may be constructed from a temperature-sensitive polymer that expands or opens in response to a change in temperature, and retracts or collapses when exposed to another temperature, such as by respective insertion and removal from the patient's oral cavity.

As in conventional laryngoscopy, the bite block 30 is preferably formed from any suitable material that will not break or harm the patient's teeth when the bite block 30 comes into contact with the teeth. The bite block 30 is preferably formed from material that will flex in response to pressure from a tooth, thus protecting the patient's teeth during placement, deployment, collapsing, and removal of the laryngoscope 10. The bite block 30 may be formed from plastic, rubber, foam, or any other suitable material.

It should be understood that the use of the laryngoscope 10 to pass an endotracheal tube 106 is shown for exemplary purposes only. As in conventional laryngoscopy, the channel 52, which is defined by the sheath 50 in the deployed state of FIG. 2, may also be used for direct, video, fiber optic, mirror/prism or camera visualization of the larynx or vocal chords of the patient. Further, the channel 52 may be used to insert an endotracheal tube 106 into the trachea T using a malleable stylet, rigid stylet, fiber optic stylet, video stylet, fiber optic scope, or the like, and may further be used to accommodate other medical devices, including, but not limited to, suction catheters, McGill forceps, double lumen endotracheal tubes, oropharyngeal tubes or nasopharyngeal tubes, esophagus scopes, surgical instruments or the like, along with providing space for laryngeal surgery and similar procedures. In general, the channel 52 may be used to pass solids, liquids or gasses through the patient's oral cavity.

Once the laryngoscope 10 is deployed, the laryngoscope 10 does not need to be manually held in place during use (i.e., when in the deployed configuration of FIG. 2), thus freeing the intubating hand of the practitioner to assist with other duties, such as laryngeal manipulation, for example. The deployment of the sheath 50 and the flexible rib 24 not only defines the channel 52, but also holds the laryngoscope 10 within the patient's oral cavity. The flexible rib 24, in the deployed state, presses against the tongue 108 and other oropharyngeal tissue, while the rigid frame 22 presses against the hard palate and opposite side of the oral cavity, the channel 52 being held open therebetween. Once the desired procedure is complete, the laryngoscope 10 may then be collapsed for easy removal, leaving the endotracheal tube 106 intact for providing oxygenation and ventilation to the patient. The laryngoscope 10 is collapsed by removing the pin 38 from the notches 40, thus allowing the proximal end 16 of the flexible rib 24 to pass back through the walls 42, 44 of the bite block 30 under the resilient force of the elastomeric sheath 50 and the flexible material forming the rib 24, along with compliance of the pharynx and the surrounding tissues, returning the laryngoscope 10 to the collapsed configuration of FIG. 1.

The laryngoscope 10, once collapsed, may alternatively be left in the oropharynx to function as a bite block and as an oral airway to displace redundant tissue while the patient is emerging from anesthesia. Further, it should be understood that the laryngoscope 10 acts as the full laryngoscopic device, although without the typical handle (such as the handle 102 in the prior art laryngoscope 100 of FIG. 3). This allows the laryngoscope to be used while still allowing an oxygen mask or the like to be placed over the patient's face. It should be understood, however, that the present laryngoscope 10 may alternatively be used in combination with an optional handle or grip portion, if desired.

Although the rigid frame 22 is shown in FIGS. 1 and 2 as being formed from a single wire or bar, it should be understood that the ribs 18, 20 may be separate and discrete components that are secured to one another at their distal ends; i.e., formed non-integrally. The rigid frame 22 may be formed from any suitable material that is rigid enough to maintain its shape when the proximal end 16 of flexible rib 24 is pulled into the deployed position of FIG. 2. It should be understood that the overall contours and relative dimensions of the rigid frame 22 may be varied, depending upon the intended use and depending upon variation in the size and shape of patients' oral cavities.

In FIGS. 1 and 2, the deployment and collapse of the laryngoscope 10 is effectuated through positioning and release of the pin 38 in the notches 40 of the walls 32, 34 of the bite block 30. It should be understood that any suitable type of alternative deployment mechanism may be used. For example, a screw-type mechanism, a pneumatic mechanism, a thermal responsive mechanism, a hydraulic mechanism, a mechanical mechanism, a pulley mechanism, a channel mechanism or an electrical mechanism may alternatively be utilized. Similarly, the deployment mechanism may alternatively be mounted on the distal end of frame 22, rather than on the proximal end thereof, as in FIGS. 1 and 2.

Further, as is well known in laryngoscopy, it should be understood that the laryngoscope 10 may be used in combination with a variety of other related tools. For example, the laryngoscope 10 may be used in combination with a light source for providing light into the channel 52, thus improving the visibility of the oropharynx, larynx or vocal chords. Still or video cameras, along with associated optics, may further be mounted on the laryngoscope 10 to capture images, for example.

It should be understood that the combination of the rigid frame 22 and the flexible rib 24 may be replaced by any other suitable type of configuration. For example, the pair of rigid ribs 18, 20 may be replaced by a frame having a first rigid rib and a second rigid rib that has a flexible tip. As a further alternative, the rigid frame may include a first rigid rib and a second rigid rib that has a camera source and/or fiber optics and/or mirrors and prisms and/or a light source integrated therewith. As a further alternative, the flexible rib 24 may be coupled to the rigid frame 22 by at least one swivel device. As another alternative, the air passage 26 formed through the flexible rib 24 may be replaced by or augmented with an air passageway formed through at least one of ribs 18, 20. The flexible rib 24 and/or at least one of ribs 18, 20 may further include a suction port, in addition to the passageway 26. As yet another alternative, the frame 22 may be provided with more than one flexible rib. The at least one flexible rib may then have integrated therein a camera source, fiber optics, prisms, mirrors, a wireless camera that projects images wirelessly to a remote monitor, or the like. These additional elements may, alternatively, be integrated into the frame 22.

As a further alternative, the rigid frame 22 may define a recess for the oropharyngeal tissue. Alternatively, the rigid frame may be formed from a pair of ribs that are coupled to one another by a bellows. In this alternative embodiment, the bellows material deploys to define the sidewalls of the channel 52. As another further alternative, the flexible rib and/or the frame may be inflatable. In still another further alternative, the flexible rib may have a helical or coiled contour.

It is to be understood that the present invention is not limited to the embodiments described above, but encompasses any and all embodiments within the scope of the following claims.

I claim:

1. A collapsible laryngoscope, comprising:
   a substantially U-shaped frame having an open proximal end, a closed distal end, and a central portion between the proximal and distal ends, the proximal and distal ends being raised with respect to the central portion;
   a bite block, the proximal end of the substantially U-shaped frame being secured thereto;
   a flexible rib having opposed proximal and distal ends, a central portion between the proximal and distal ends, and an upper surface, the distal end of the flexible rib being secured to the distal end of the substantially U-shaped frame;
   an elastomeric sheath secured to and covering the substantially U-shaped frame and the upper surface of the central portion of the flexible rib; and
   means for lifting the central portion of the flexible rib with respect to the substantially U-shaped frame;
   whereby the substantially U-shaped frame is adapted for insertion into a patient's oral cavity with the flexible rib being in a collapsed state and the central portion of the flexible rib being aligned with the central portion of the substantially U-shaped frame, the flexible rib then being liftable with respect to the substantially U-shaped frame such that the elastomeric sheath and the flexible rib press against the patient's tongue and oropharyngeal tissue and the substantially U-shaped frame press against the patient's hard palate, so that the elastomeric sheath defines an open channel beneath the flexible rib.

2. The collapsible laryngoscope as recited in claim 1, wherein said flexible rib has an air passage defined therethrough.

3. The collapsible laryngoscope as recited in claim 1, wherein said means for lifting the central portion of said flexible rib with respect to said substantially U-shaped frame comprises a strap secured to the proximal end of said flexible rib.

4. The collapsible laryngoscope as recited in claim 3, wherein said bite block comprises a central portion and a pair of opposed sidewalls.

5. The collapsible laryngoscope as recited in claim 4, wherein the proximal end of said flexible rib extends between the pair of opposed sidewalls of said bite block, said flexible rib being lifted with respect to said substantially U-shaped frame when the proximal end is pulled through the sidewalls of said bite block.

6. The collapsible laryngoscope as recited in claim 5, further comprising means for locking said flexible rib in a deployed, lifted position.

7. The collapsible laryngoscope as recited in claim 6, wherein:
said bite block has a pair of notches formed in the opposed sidewalls; and
said means for locking said flexible rib in the deployed, lifted position comprises a pin secured to the proximal end of said flexible rib, the pin releasably engaging the notches.

8. A collapsible laryngoscope, comprising:
a substantially U-shaped frame having an open proximal end, a closed distal end, and a central portion extending between the proximal and distal ends, the proximal and distal ends being raised with respect to the central portion;
a bite block, the proximal end of the substantially U-shaped frame being secured thereto;
a flexible rib having opposed proximal and distal ends, a central portion extending between the proximal and distal ends, and an upper surface, the distal end of the flexible rib being secured to the distal end of the substantially U-shaped frame;
an elastomeric sheath secured to and covering the substantially U-shaped frame and the upper surface of the central portion of the flexible rib; and
a strap secured to the proximal end of the flexible rib for lifting the central portion of the flexible rib with respect to the substantially U-shaped frame;
whereby the substantially U-shaped frame is adapted for insertion into a patient's oral cavity with the flexible rib being in a collapsed state and the central portion of the flexible rib being aligned with the central portion of the substantially U-shaped frame, the flexible rib being lifted with respect to the substantially U-shaped frame when the strap is pulled so that the elastomeric sheath and the flexible rib press against the patient's tongue and oropharyngeal tissue and the substantially U-shaped frame presses against the patient's hard palate, the elastomeric sheath defining an open channel beneath the flexible rib.

9. The collapsible laryngoscope as recited in claim 8, wherein said flexible rib has an air passage defined therethrough.

10. The collapsible laryngoscope as recited in claim 9, wherein said bite block comprises a central portion and a pair of opposed sidewalls.

11. The collapsible laryngoscope as recited in claim 10, wherein the proximal end of said flexible rib extends between the pair of opposed sidewalls of said bite block, said flexible rib being lifted with respect to said substantially U-shaped frame when the proximal end of said flexible rib is being pulled through the sidewalls.

12. The collapsible laryngoscope as recited in claim 11, further comprising means for locking said flexible rib in a deployed, lifted position.

13. The collapsible laryngoscope as recited in claim 12, wherein:
said bite block has a pair of notches formed in the opposed sidewalls; and
said means for locking said flexible rib in the deployed, lifted position comprises a pin secured to the proximal end of said flexible rib, the pin releasably engaging the notches.

14. A collapsible laryngoscope, comprising:
a substantially U-shaped frame having an open proximal end, a closed distal end, and a central portion extending between the proximal and distal ends, the proximal and distal ends being raised with respect to the central portion;
a bite block, the proximal end of the substantially U-shaped frame being secured thereto;
a flexible rib having opposed proximal and distal ends, a central portion extending between the proximal and distal ends, and an upper surface, the distal end of the flexible rib being secured to the distal end of the substantially U-shaped frame;
an elastomeric sheath secured to and covering the substantially U-shaped frame and the upper surface of the central portion of the flexible rib;
a strap secured to the proximal end of the flexible rib for lifting the central portion of the flexible rib with respect to the substantially U-shaped frame; and
means for locking the flexible rib in a deployed, lifted position;
whereby the substantially U-shaped frame is adapted for insertion into a patient's oral cavity with the flexible rib being in a collapsed state and the central portion of the flexible rib being aligned with the central portion of the substantially U-shaped frame, the flexible rib being liftable with respect to the substantially U-shaped frame when the strap is pulled so that the elastomeric sheath and the flexible rib press against the patient's tongue and oropharyngeal tissue and the substantially U-shaped frame presses against the patient's hard palate, the elastomeric sheath defining an open channel beneath the flexible rib.

15. The collapsible laryngoscope as recited in claim 14, wherein said flexible rib has an air passage defined therethrough.

16. The collapsible laryngoscope as recited in claim 15, wherein said bite block comprises a central portion and a pair of opposed sidewalls.

17. The collapsible laryngoscope as recited in claim 16, wherein the proximal end of said flexible rib extends between the pair of opposed sidewalls of said bite block, said flexible rib being lifted with respect to said substantially U-shaped frame when the proximal end of said flexible rib is pulled through the sidewalls.

18. The collapsible laryngoscope as recited in claim 17, wherein:
   said bite block has a pair of notches formed in the opposed sidewalls; and
   said means for locking said flexible rib in the deployed, lifted position comprises a pin secured to the proximal end of said flexible rib, the pin releasably engaging the notches.

* * * * *